United States Patent
Ji et al.

(10) Patent No.: US 9,925,570 B2
(45) Date of Patent: Mar. 27, 2018

(54) OPEN PATH OPTICAL SENSING SYSTEM HAVING AN ULTRASONIC CLEANER AND METHOD

(71) Applicant: NEC Laboratories America, Inc., Princeton, NJ (US)

(72) Inventors: Philip Ji, Plainsboro, NJ (US); Ting Wang, West Windsor, NJ (US)

(73) Assignee: NEC Corporation, Tokyo (JP)

( * ) Notice: Subject to any disclaimer, the term of this patent is extended or adjusted under 35 U.S.C. 154(b) by 268 days.

(21) Appl. No.: 14/949,261

(22) Filed: Nov. 23, 2015

(65) Prior Publication Data

US 2016/0146721 A1    May 26, 2016

Related U.S. Application Data (60) Provisional application No. 62/084,851, filed on Nov. 26, 2014.

(51) Int. Cl.
  *B08B 7/02* (2006.01)
  *G01N 21/15* (2006.01)
  *B08B 17/02* (2006.01)

(52) U.S. Cl.
  CPC .............. *B08B 7/028* (2013.01); *B08B 17/02* (2013.01); *G01N 21/15* (2013.01); *G01N 2021/154* (2013.01)

(58) Field of Classification Search
  CPC ........ B08B 7/028; B08B 17/02; G01N 21/15; G01N 2021/154
  See application file for complete search history.

(56) References Cited

U.S. PATENT DOCUMENTS

| | | | |
|---|---|---|---|
| 4,768,256 A | 9/1988 | Motoda | |
| 5,172,024 A * | 12/1992 | Broussoux | ............ B06B 1/0688 310/321 |
| 8,899,761 B2 * | 12/2014 | Tonar | ................. G02B 27/0006 359/509 |

FOREIGN PATENT DOCUMENTS

| | | |
|---|---|---|
| CN | 203142624 U | 8/2013 |
| CN | 203599160 U | 5/2014 |
| DE | 20 2004 019 608 U1 | 3/2005 |
| DE | 10 2011 107 871 A1 | 1/2013 |

(Continued)

OTHER PUBLICATIONS

"Advantages of the LI-7700 Open Path CH4 Analyzer" Accessed online Sep. 22, 2015, 3 pages.

*Primary Examiner* — Saeed T Chaudhry
(74) *Attorney, Agent, or Firm* — Joseph Kolodka (57) ABSTRACT

An open path optical sensing system having an ultrasonic cleaner. The system includes at least one ultrasound transducer which is configured to propagate ultrasonic waves across exposed surfaces of optical components of the optical sensing system. The ultrasonic waves create tiny vibrations on the exposed surfaces of the optical components which clean the surfaces of environmental pollutants and prevent environmental pollutants from accumulating on the surface. The ultrasonic waves may have a frequency that is substantially different than the modulation frequency of a modulated laser light beam that is generated by a laser of the open path optical sensing system. The surfaces of a plurality of optical components may be cleaned by the ultrasonic waves of a single ultrasound transducer. A plurality of ultrasound transducers may propagate waves on a single optical component.

20 Claims, 10 Drawing Sheets

(56) References Cited

FOREIGN PATENT DOCUMENTS

EP     2 332 791 A1    6/2011
WO    2012/095643 A1   7/2012

* cited by examiner

OPEN PATH OPTICAL SENSING SYSTEM HAVING AN ULTRASONIC CLEANER AND METHOD

RELATED APPLICATION INFORMATION

This application claims priority to provisional application Ser. No. 62/084,851 filed on Nov. 26, 2014, incorporated herein by reference.

BACKGROUND

Technical Field

The present invention relates to optical sensing systems, and more particularly, systems and methods for cleaning open path optical sensing systems.

Description of the Related Art

Optical sensing systems are utilized for a wide range of applications including gas and particle sensing and detection. One type of optical particle sensing and detection is open path absorption spectroscopy. In open path absorption spectroscopy, an optical source and a receiver are placed in the same environment as a gas to be measured. A light, such as a laser or LED, is directed by the optical source directly through the gaseous environment. The different types of gases in the environment will cause the light to absorb at different wavelengths. The absorbed light is received by the receiver and is measured and analyzed to discover the type of gases that are present and their respective concentrations.

Examples of open path absorption spectroscopy systems, include Tunable Diode Laser Absorption Spectroscopy (TDLAS), Intra-Cavity Absorption Spectroscopy (ICAS), and Cavity-Ring Down Spectroscopy (CRDS).

A main disadvantage of open path absorption spectroscopy is that the surfaces of some optical components are exposed to environmental pollutants which lead to a degradation of the performance of the system. For example, the optical components may exhibit a poorer reflection, poorer transparency or a sensor malfunction due to the environmental pollutants. Prior art systems have been provided with higher quality surface materials and an improved build quality in order to reduce potential pollutants from contacting the surface of the system. However, these systems have only provided marginal benefits with respect to the accumulation of pollutants.

Other prior art systems have featured mechanical wiping mechanisms, such as wipers, that are configured to wipe pollutants from the surface of the optical components. However, the mechanical wiping mechanisms are susceptible to inadvertently damaging the optical components and may also affect the performance of the sensor. Furthermore, the mechanical wiping mechanisms require continual replacement.

Other prior art systems have been developed which wash the surface of the optical components in order to remove pollutants. For example, a stream of washer fluid may be directed onto the surface of an optical component and the surface may be rotated. The surfaces of the washed components are then dried. However, in these systems, the sensors are unable to function during the cleaning and drying periods. The cleaning solution may also leave a residue which can degrade the performance of the optical system. Furthermore, these systems require additional structures to operate, such as electrical power and a water supply.

Therefore, a system and method for cleaning open path optical sensors which effectively cleans the optical component surfaces and prevents a build-up of pollutants which does not damage the surface of the optical component, does not require replacement of parts that are subject to frequent degradation, does not require the use of a cleaning fluid, and allows constant operation of the optical sensor would be highly advantageous.

SUMMARY

A method for cleaning optical components of an open path optical sensing system which includes the step of positioning at least one ultrasound transducer near a surface of at least one of the plurality of optical components, wherein the surface is exposed to environmental pollutants. The method further includes the step of propagating ultrasonic waves across the surface by the at least one ultrasound transducer to clean the surface of environmental pollutants and prevent environmental pollutants from accumulating on the surface.

An open path optical sensing system which includes a plurality of optical components wherein at least one of the plurality of optical components has a surface that is exposed to environmental pollutants. The system includes at least one ultrasound transducer positioned near the surface of at least one of the plurality of optical components. The ultrasound transducer is configured to propagate ultrasonic waves across the surface to clean the surface of environmental pollutants and prevent environmental pollutants from accumulating on the surface.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

In accordance with the present principles, systems and methods are provided for an open path optical sensing system having an ultrasonic cleaner. The system includes at least one ultrasound transducer which is configured to propagate ultrasonic waves across exposed surfaces of the optical sensing system. The ultrasonic waves create tiny vibrations on the exposed surfaces of the optical components which clean the surfaces of environmental pollutants and prevent environmental pollutants from accumulating on the surface. The system ensures that the optical components of the optical sensing system are clean in order to provide improved operational performance and an increased lifespan of the optical sensing system. The ultrasonic cleaner does not require a cleaning solution or mechanical moving parts. Furthermore, the ultrasonic cleaner can operate continually without requiring the open path optical sensing system to be shut down and the ultrasonic cleaner does not interfere with the operation of the system.

Embodiments described herein may be entirely hardware, entirely software or may include both hardware and software elements which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Figure 1:
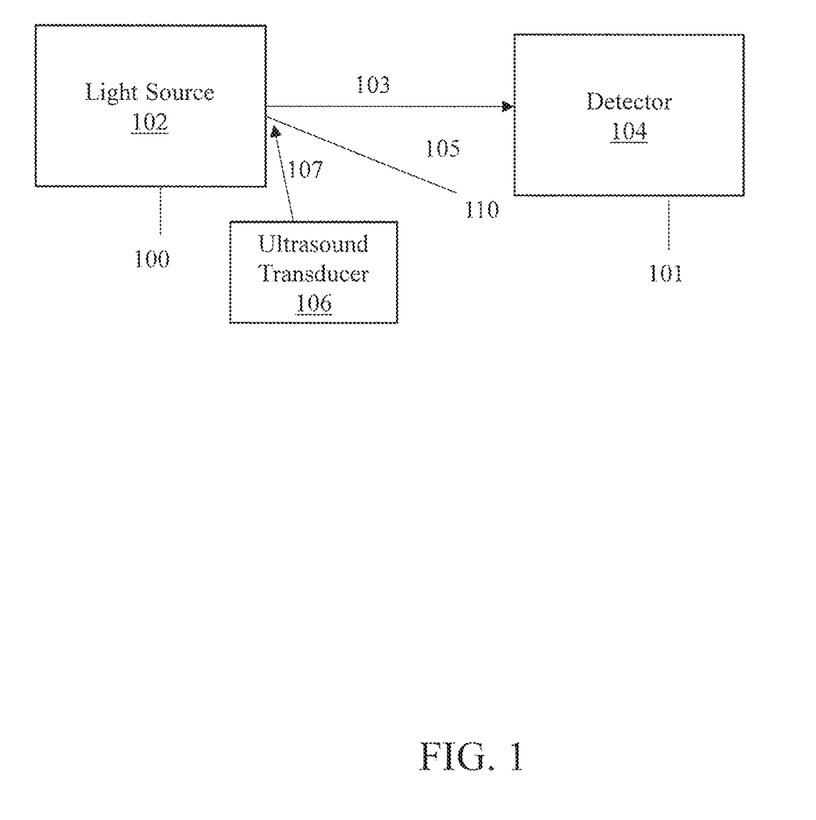
FIG. 1 is a block/flow diagram illustratively depicting an open path optical sensing system featuring an ultrasonic cleaner in accordance with the present principles.

Referring now to the drawings in which like numerals represent the same or similar elements and initially to FIG. 1, a block/flow diagram depicting an open path optical sensing system 100, is illustratively shown in accordance with one embodiment of the present principles. The system 100 may include a plurality of optical components 101. The optical components 101 may include a light source 102 and a detector 104. The system may include one or more ultrasound transducers 106 that are positioned in proximity to optical components of the optical sensing system 100 that are exposed to environmental pollutants. The ultrasound transducers emit surface acoustic waves which are ultrasonic waves that are propagated across the exposed surfaces 110 of the optical components.

For example, in one embodiment, at least one ultrasound transducer 106 may be positioned at an edge of the surface of an optical component in order to emit surface acoustic waves. In alternative embodiments, the ultrasound transducer 106 may be mounted on a structure on or near an optical component that has a surface that is exposed to environmental pollutants so that the ultrasound transducer emits surface acoustic waves which propagate across the surface of the optical component.

In one embodiment, the ultrasound transducers 106 may be piezoelectric transducers which include a piezoelectric crystal that is configured to change size when a voltage is applied. In other embodiments the ultrasound transducers 106 may be a capacitive transducer which uses electrostatic fields between a conductive diaphragm and a backing plate to generate an ultrasonic wave. Other ultrasound transducers 106 known in the art may also be utilized in accordance with the present principles.

The ultrasound transducers 106 are configured to convert electrical energy into acoustic ultrasonic waves. The ultrasound transducers 106 are configured to generate ultrasonic waves at a wide range of ultrasonic frequencies. For example, in certain embodiments the ultrasound transducers 106 may generate ultrasonic waves having a frequency of 30 kHz. However, the ultrasound transducers 106 may be configured to generate ultrasonic waves at any other ultrasound frequency as may be desired.

In a preferred embodiment, the ultrasound transducers 106 may be configured to generate ultrasonic waves on a constant basis so that surface acoustic waves are continually propagated across the exposed surfaces of the optical components. However, in other embodiments, the ultrasound transducers may include a control module which may stop the propagation of ultrasound waves by the ultrasound transducers at intervals specified by the user to allow ultrasound transducers to generate ultrasonic waves on a timed basis. The control module may be integrated within the ultrasound transducers or may be a separate device connected to the ultrasound transducer, as generally known in the art.

The ultrasonic waves propagated by the ultrasound transducers 106 across the surfaces 110 of the optical components create tiny vibrations on the exposed surfaces which cause large rain drops to break up into microscopic droplets that are very light and can be easily bounced off or blown away. The ultrasonic waves also loosen dirt particles and cause pollutants, including, but not limited to, dust, dirt particles, mud, rain drops, insects and other foreign objects ("Pollutants") from accumulating on the surfaces 110 of the optical components.

Figure 2:
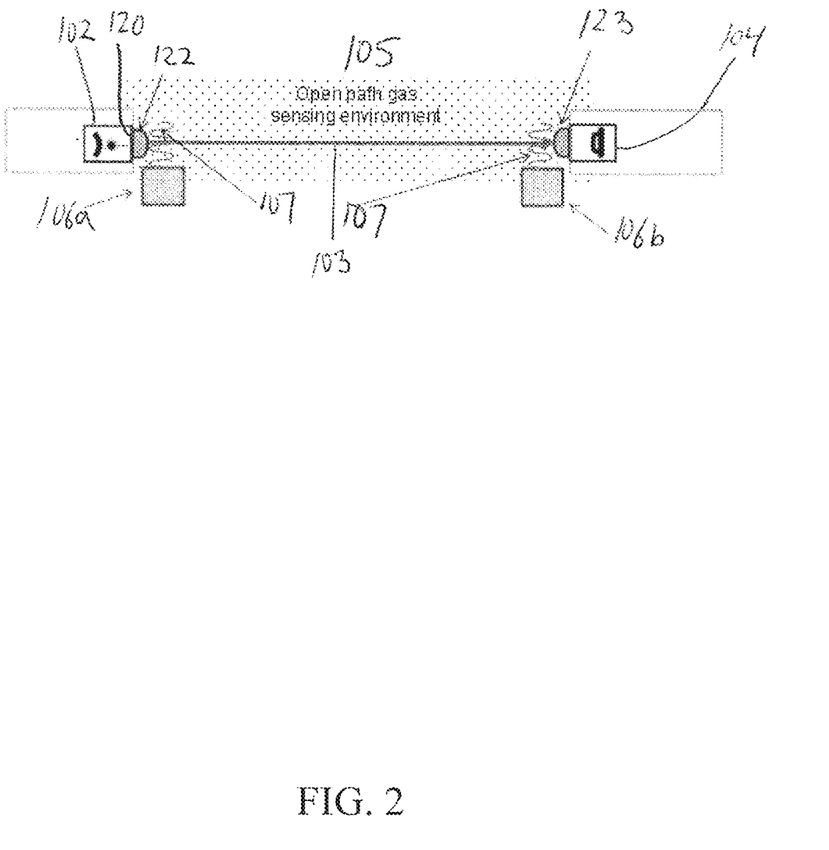
FIG. 2 is a block/flow diagram illustratively depicting a single pass open path optical sensing system featuring an ultrasonic cleaner in accordance with the present principles.
Figure 3:
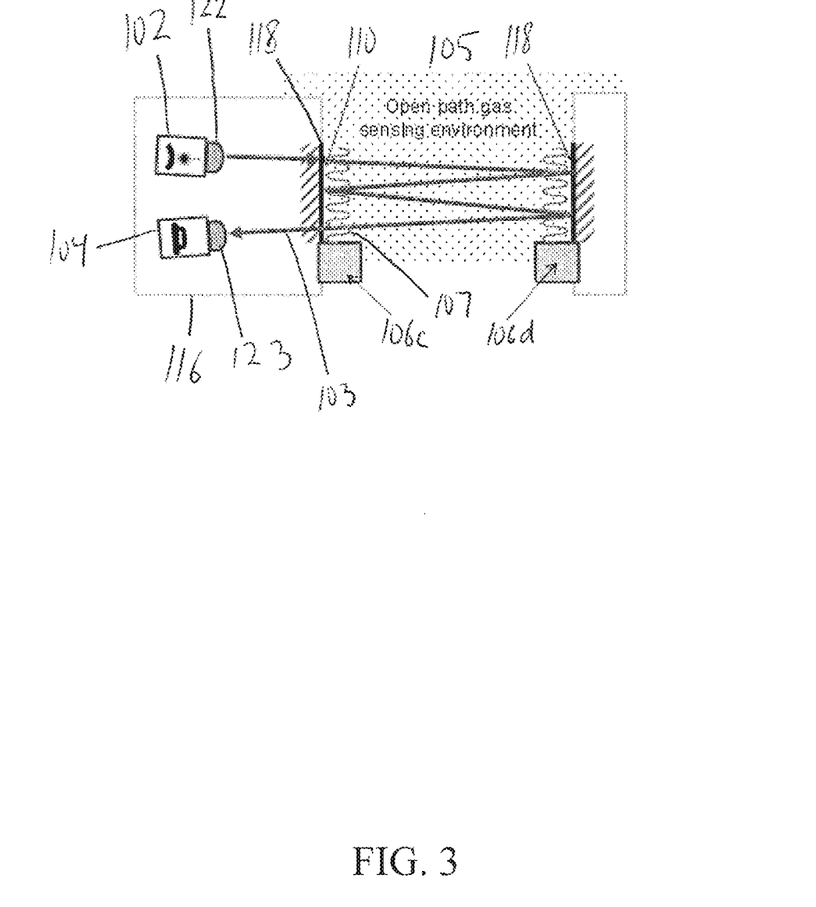
FIG. 3 is a block/flow diagram illustratively depicting a multi-pass open path optical sensing system featuring an ultrasonic cleaner in accordance with the present principles.
Figure 4:
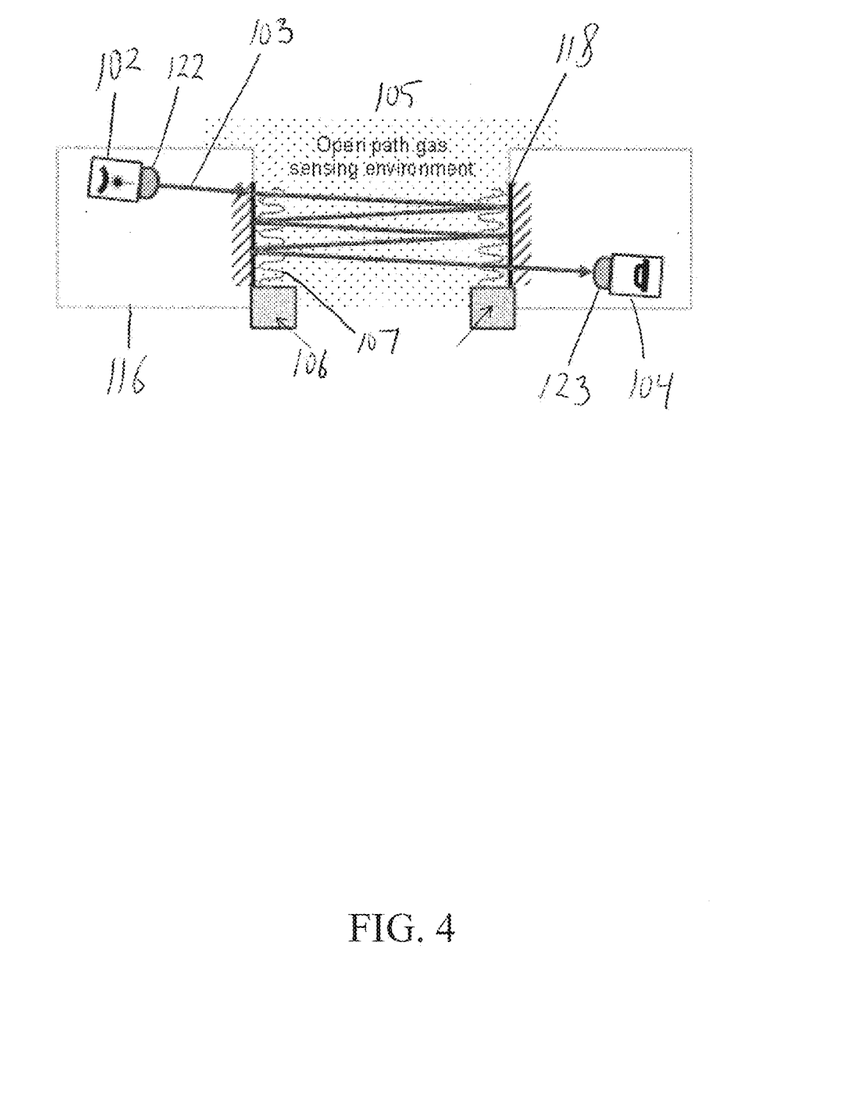
FIG. 4 is a block/flow diagram illustratively depicting another embodiment of a multi-pass open path optical sensing system featuring an ultrasonic cleaner in accordance with the present principles.
Figure 5:
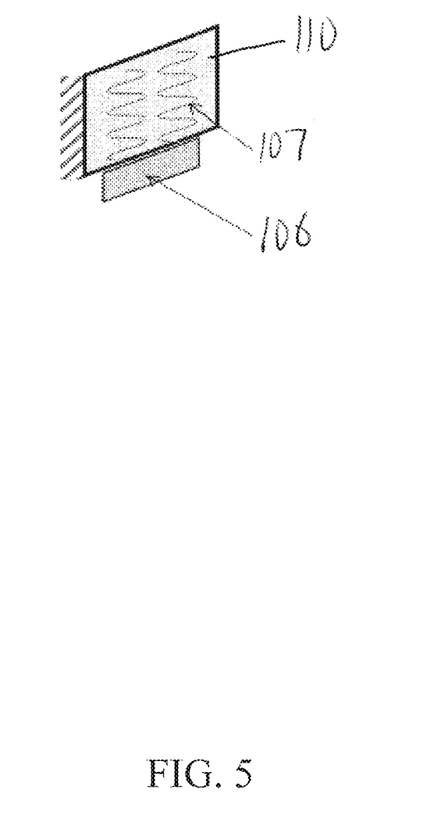
FIG. 5 is a diagram illustratively depicting an ultrasound transducer and an optical component in accordance with the present principles.
Figure 6:
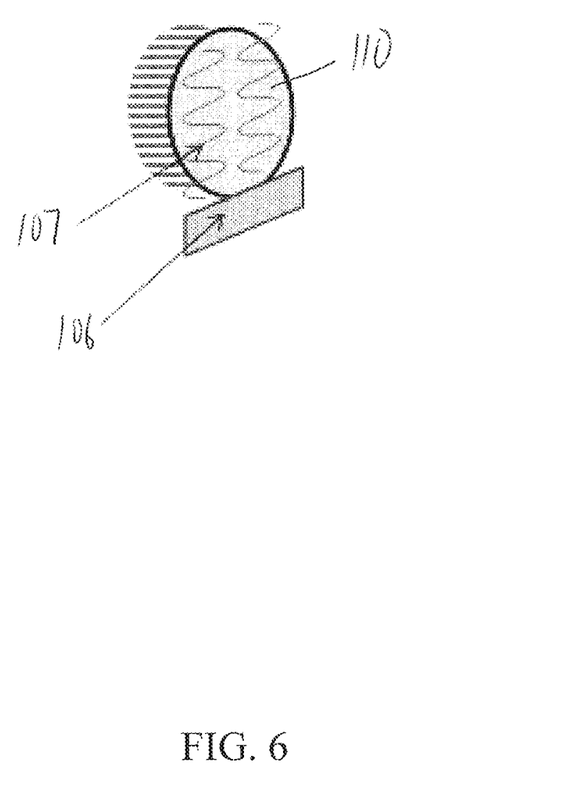
FIG. 6 is a diagram illustratively depicting another embodiment of an ultrasound transducer and an optical component in accordance with the present principles.

The embodiment shown in FIGS. 2-4 show open path optical sensing systems which are open path absorption spectroscopy systems featuring an ultrasonic cleaner. These illustrative embodiments include a light source 102, such as a laser, a detector 104 and a plurality of ultrasound transducers 106. The light source 102 may include a transparent/ translucent cover 120, such as a glass plate. The light source 102 may further include a lens 122 to collimate the light and direct the light from the light source to the intended target. The detector 104 may also include a lens 123 to receive the light.

The embodiment shown in FIG. 2 is a single pass absorption spectroscopy sensor system. In a single pass absorption spectroscopy sensor system 114, light from the light source is passed through the gas environment 105 only once before it is received by the detector 104.

The embodiments shown in FIGS. 3-4 show multi-pass open path absorption spectroscopy systems 116. In multi-pass open path absorption spectroscopy systems 116, the light is reflected back and forth multiple times before being received by the detector 104. The multi-pass systems include mirrors 118 to reflect the light beam back and forth. In the embodiment shown in FIG. 3, the light source 102 and the detector 104 are positioned on the same side. The light 103 emitted by the light source is reflected three times before the light is received by the detector 104. In the embodiment shown in FIG. 4, the light source 102 and the detector 104 are positioned on opposite sides. The light 103 emitted by the light source is reflected four times by the mirrors 118 before the light is received by the detector 104.

As shown in FIGS. 2-4, a plurality of ultrasound transducers 106 may be utilized to clean the surfaces of the optical components. For example, in FIG. 2, the system includes a first ultrasound transducer 106a that is positioned in proximity to the lens 122 of the light source to clean the surface of the lens. A second ultrasound transducer 106b is positioned in proximity to the lens 123 of the detector to clean the surface of this optical component. In FIGS. 3-4, a pair of ultrasound transducers 106c, 106d are utilized to clean the surfaces of the mirrors 118 on opposing sides of the system.

However, in other embodiments, the ultrasound transducers 106 may be positioned in proximity to any component of the open path optical sensing system that has a surface that is exposed to Pollutants or requires cleaning. For example, the ultrasound transducers 106 may be positioned in proximity to the transparent/translucent cover 120 of the light source. Additionally, the ultrasound transducers 106 may be positioned in proximity to a fiber collimator that directs the light from a fiber which carries the light from a remote light source. The ultrasound transducer may also be positioned in proximity to a fiber collimator that collects and focuses the light into a fiber that carries the light to a remote receiver.

Figure 7:
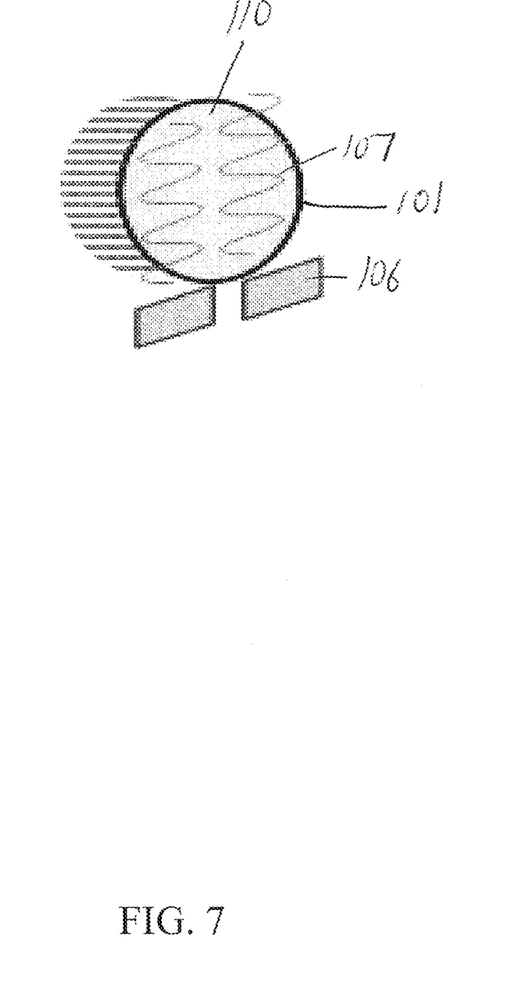
FIG. 7 is a diagram illustratively depicting a plurality of ultrasound transducers and an optical component in accordance with the present principles.
Figure 8:
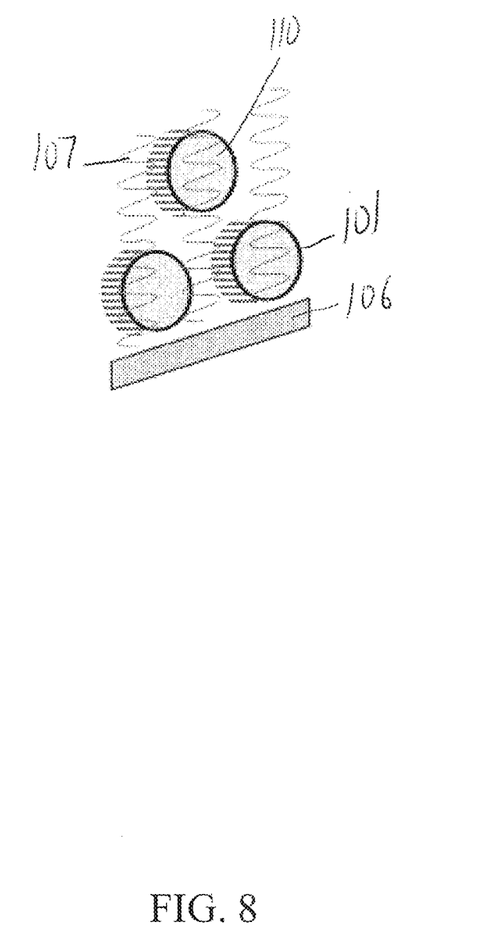
FIG. 8 is a diagram illustratively depicting an ultrasound transducer and a plurality of optical components in accordance with the present principles.

As shown in FIGS. 5-8, the surfaces of the ultrasound transducers 106 may have different shapes, such as rectilinear or spherical shapes and may be sized with a wide variety of dimensions, as necessary. Furthermore, as shown in FIG. 7, a plurality of ultrasound transducers 106 may be utilized to propagate ultrasonic waves 107 across a surface 110 of one optical component 101. Alternatively, as shown in FIG. 8, one ultrasound transducer 106 may be utilized to propagate ultrasonic waves 107 across the surfaces 110 of a plurality of optical components 101.

The positioning of the ultrasound transducers 106 may be adjusted to ensure that the ultrasonic waves 107 propagate across the exposed surface 110 of the optical component. Factors that may influence the positioning of the ultrasound transducer 106 include the active transducer area and shape, the propagation medium and the frequency of the ultrasonic waves.

Figure 9:
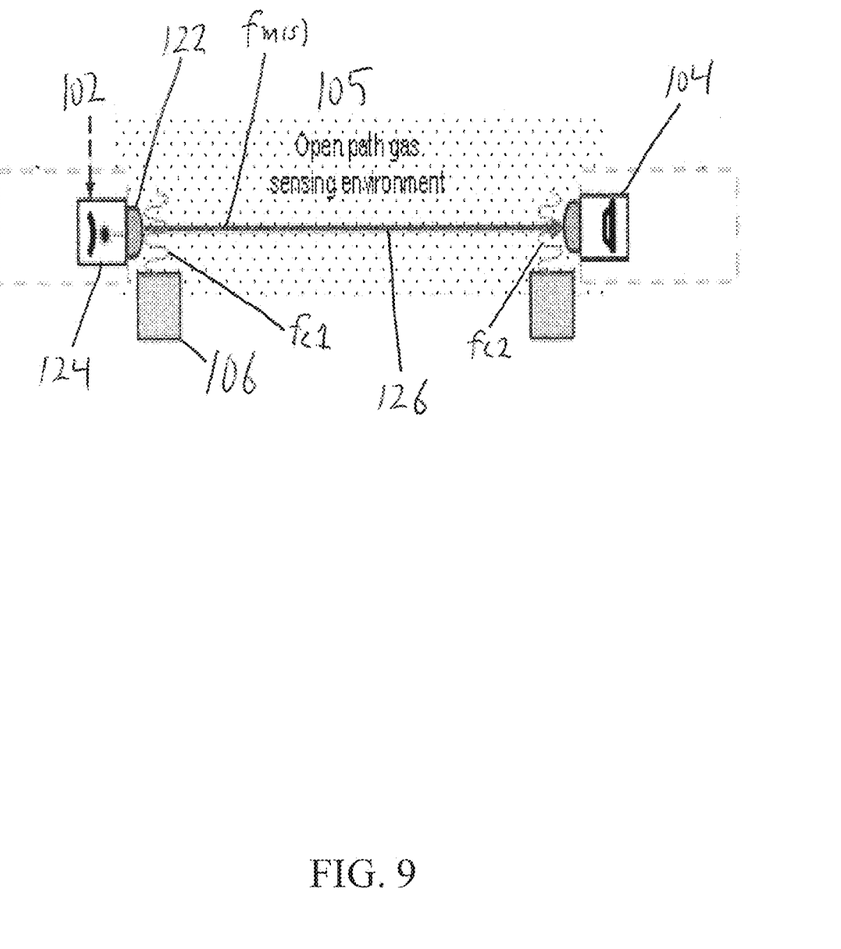
FIG. 9 is a block/flow diagram illustratively depicting another embodiment of a single pass open path optical sensing system featuring an ultrasonic cleaner in accordance with the present principles.

As shown in FIG. 9, in a preferred embodiment, the light source 102 is a laser 124. The laser 124 is configured to produce laser light signals 126 having a specific wavelength. The signal 126 produced by the laser may be modified by a modulator. For example, a commonly used technique to improve the sensor sensitivity is to apply modulation to the optical signal at the transmitter. The modulation raises the frequency of the signal to remove noise and filter out the signal. Additionally, the laser 124 may perform frequency-division multiplexing wherein the laser signal 126 combines a plurality of different laser signals that are modulated at different frequencies. The multiplexed laser signal is then de-modulated into separate laser signals.

While the wavelength of an ultrasonic wave is typically very different than the wavelength of a light signal 126, the modulation frequency of a modulated laser signal may be similar to the frequency of the ultrasonic wave. In order to avoid noise and cross-talk between the ultrasonic wave 107 and the frequency of a modulated laser, the frequencies of the ultrasonic waves 107 produced by the ultrasound transducers are configured to be a different frequency than the modulation frequencies of the laser light signals 126 produced by the laser. For example, in FIG. 9, the frequencies $f_{c1}$ and $f_{c2}$ of the ultrasonic waves emitted by the ultrasound transducers 106 are configured to be substantially different than the frequency of the laser light signal 126 $f_{m(s)}$. In certain embodiments, the system 100 may include a frequency detector to determine the modulation frequency of modulated laser light signals 126 and a control unit may be configured to change the frequency of the ultrasonic waves 107 to differentiate the frequency from the frequency of the modulated laser light signals.

While the system 100 is described with respect to open path absorption spectroscopy systems, the system may be used for any other type of open path optical sensing system which includes exposed components, including, but not limited to, scattering-based optical sensors (such as PM2.5 detectors), backscattering-based optical sensors (such as Light Detection and Ranging systems), emission-based optical sensors (such as hyperspectral imaging systems), and other open path optical sensing systems known in the art. The system 100 may be used for optical sensing systems that are configured for a wide variety of applications including distance sensing, free space temperature sensing, hyperspectral imaging, etc.

Figure 10:
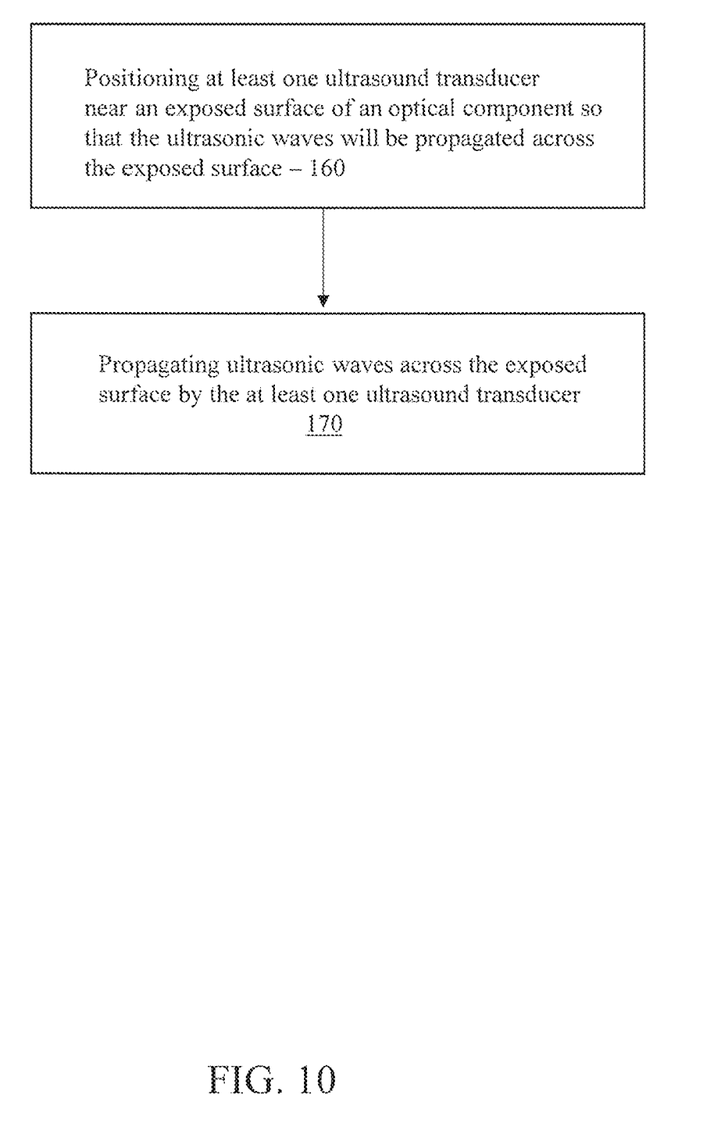
FIG. 10 is a flow diagram showing a method for cleaning the surfaces of optical components of an open path optical sensing system by at least one ultrasound transducer in accordance with the present principles.

As shown in FIG. 10, the present invention is also directed to methods for cleaning exposed surfaces of optical components of an open path optical sensing system by an ultrasonic cleaner. The method may be performed by any combination of hardware and/or software.

Referring to FIG. 10, a method for cleaning optical components of an open path optical sensing system by an ultrasonic cleaner is illustratively shown in accordance with the present principles. In block 160, at least one ultrasound transducer is positioned near an exposed surface of an optical component of the open path optical sensing system so that the ultrasonic waves will be propagated across the exposed surface of the optical component. In block 170, the ultrasound transducer propagates ultrasonic waves across the exposed surface in order to remove Pollutants and/or prevent the accumulation of Pollutants on the surface. In embodiments wherein the optical sensing system includes a laser, the ultrasonic waves are preferably emitted at a frequency that is substantially different from the frequency of the modulated laser beam generated by the laser.

While the above configuration and steps are illustratively depicted according to one embodiment of the present principles, it is contemplated that other sorts of configurations and steps may also be employed according to the present principles. While various components have been illustratively described as separate components, the components may be formed in a variety of integrated hardware or software configurations.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A method for cleaning optical components of an open path optical sensing system, comprising the steps of:
    positioning at least one ultrasound transducer near a fiber collimator or fiber that directs light from a fiber which carries light from a remote light source to at least one of a plurality of optical components exposed to environmental pollutants; and
    propagating ultrasonic waves across the surface by said at least one ultrasound transducer to clean the surface of environmental pollutants and prevent environmental pollutants from accumulating on a surface.

2. The method as recited in claim 1, wherein:
    the open path optical sensing system is an open path absorption spectroscopy system; and
    the plurality of optical components includes a light source and a detector.

3. The method as recited in claim 2, wherein ultrasonic waves are propagated across the surface of at least one of the following optical components: a lens of the light source, a lens of the detector, a transparent/translucent cover of the light source, a mirror.

4. The method as recited in claim 1, further comprising the step of utilizing ultrasound transducers having a size and shape that provide sufficient ultrasonic waves across the surface to clean the surface and prevent environmental pollutants from accumulating on the surface.

5. The method as recited in claim 1, comprising the step of propagating ultrasonic waves by the ultrasound transducer, wherein said ultrasonic waves have a frequency that is substantially different than the modulation frequency of a modulated laser light beam that is generated by a laser of the open path optical sensing system.

6. The method as recited in claim 1, comprising the step of propagating ultrasonic waves by a first ultrasound transducer, wherein said ultrasonic waves travel across exposed surfaces of a plurality of optical components.

7. The method as recited in claim 1, comprising the step of propagating ultrasonic waves by a plurality of ultrasound transducers, wherein said ultrasonic waves travel across a first surface of a first optical component.

8. The method as recited in claim 1, comprising the step of propagating ultrasonic waves across the surface on a continual basis.

9. The method of claim 1, comprising reflecting light generated by an optical emitter in multiple passes (multi-pass) and receiving at an optical detector and positioning the transducer in proximity to a fiber collimator.

10. The method of claim 1, comprising adjusting a position of the transducer based on transducer area, propagation medium and frequency.

11. The method of claim 1, comprising modulating a laser signal, wherein the frequency of the transducer's ultrasonic wave is proximal to a modulated frequency of the laser signal.

12. The method of claim 1, comprising modulating a laser signal, wherein the frequency of the transducer's ultrasonic wave is different from a modulated frequency of the laser signal.

13. An open path optical sensing system, comprising:
    a plurality of optical components wherein at least one of the plurality of optical components has a surface that is exposed to environmental pollutants; and
    at least one ultrasound transducer positioned near the fiber collimator that directs light from a fiber which carries light from a remote light source or fiber, said at least one ultrasound transducer configured to propagate ultrasonic waves across the surface.

14. The open path optical sensing system of claim 13, wherein:
    the system is an open path absorption spectroscopy system; and
    the plurality of optical components includes a light source and a detector.

15. The open path optical sensing system of claim 14, wherein the at least one
    ultrasound transducer is configured to clean optical components comprising at least one of: a lens of the light source, a lens of the detector, a transparent/translucent cover, a mirror.

16. The open path optical sensing system of claim 14, wherein the size and shape of the ultrasound transducer are configured to provide sufficient ultrasonic waves across the surface to clean the surface and prevent environmental pollutants from accumulating on the surface.

17. The open path optical sensing system of claim 14, wherein:
    the light source is a laser that is configured to generate a modulated laser light beam; and
    the ultrasound transducer is configured to produce ultrasonic waves having a frequency that is substantially different than the modulation frequency of the modulated laser light beam that is generated by the laser.

18. The open path optical sensing system of claim 13, wherein a first ultrasound transducer is configured to propagate ultrasonic waves across surfaces of a plurality of optical components.

19. The open path optical sensing system of claim 13, wherein a plurality of ultrasound transducers are configured to propagate ultrasonic waves across a first surface of a first optical component.

20. The open path optical sensing system of claim 13, wherein the at least one ultrasound transducer is configured to propagate ultrasonic waves across the exposed surface on a continual basis.

* * * * *